United States Patent [19]
Dahm et al.

[11] Patent Number: 5,912,730
[45] Date of Patent: Jun. 15, 1999

[54] SPECTROGRAPHIC ANALYSIS INSTRUMENT AND METHOD BASED ON DISCONTINUUM THEORY

[75] Inventors: Donald J. Dahm, Ludlow; Kevin D. Dahm, Somerville, both of Mass.

[73] Assignee: Foss NIRSytems, Inc., Silver Spring, Md.

[21] Appl. No.: 08/964,021

[22] Filed: Nov. 4, 1997

[51] Int. Cl.$^6$ .................................................. G01N 21/00
[52] U.S. Cl. .............................. 356/72; 356/73; 356/381; 356/432; 356/357
[58] Field of Search ................................ 356/72, 73, 381, 356/432, 357

Primary Examiner—Frank G. Font
Assistant Examiner—Reginald A. Ratliff
Attorney, Agent, or Firm—Lane, Aitken & McCann

[57] ABSTRACT

In a method and apparatus for analyzing an unknown material, the spectra of absorption and remission coefficients are determined by means of equations relating to remission, absorption and transmission fractions through layers of material of different thicknesses in accordance with a discontinuum theory. To determine the concentration of an absorber in an unknown material, the absorption coefficients are determined for the unknown material and for samples of known material. The concentrations of absorbers in the unknown material are determined from the absorption coefficients by regression analysis.

13 Claims, 2 Drawing Sheets

SPECTROGRAPHIC ANALYSIS INSTRUMENT AND METHOD BASED ON DISCONTINUUM THEORY

This invention relates to an improved method and apparatus for determining the absorption coefficient and the remission coefficient of a material at specific wavelengths of a spectrum from remission and/or transmission measurements made on the material and to a method and apparatus for analyzing the material based on the absorption and remission coefficient determinations made from the sample.

BACKGROUND OF THE INVENTION

Near infrared spectrographic instruments are used to provide analysis of materials in order to determine the measurable characteristics of materials such as concentrations of the constituents of the materials or physical characteristics of the materials. For example, near infrared spectrographic instruments are used in agriculture to determine the oil, protein, and moisture content of grain, the fat content of meat, the fat, protein and lactose content of milk and the urea content of milk. In addition, near infrared spectrophotometer are used to analyze blood samples and to analyze pharmaceutical samples. The instruments have also been used to measure physical properties or physical characteristics of materials. For example, the instruments have been successfully used to measure the hardness of wheat.

In typical systems of the prior art, linear regressions are used to estimate analyte concentrations or other measurable characteristics from spectroscopic data, even though the raw data are clearly not linear with respect to concentration. Typically, a mathematical pretreatment is applied to the measured spectral data in an attempt to linearize it. The function log (1/R) is an empirical example of such pretreatment applied to remission measurements. The log (1/R) values can be represented in the equations summing products of the log (1/R) values and weighting coefficients or summing products of derivatives of the log (1/R) values and weighting coefficients. To determine concentrations of the constituents of unknown material, log (1/R) values of a multiplicity of known sample materials similar to the unknown material are measured by the spectrographic instrument. The concentrations of the constituents of the known sample materials are known. From the measurements made on the multiplicity of sample materials, the weighting coefficients of the equations relating the analyte concentrations to the pretreated remission measurements can be determined by multiple regression or partial least squares regression. After the coefficients have been determined, the unknown material can be analyzed by the spectrographic instrument using the coefficients that have been determined from the known sample materials. Transmission measurements are also used to analyze materials in a similar manner.

In modern instruments, the measurements on the samples are made at wavelengths distributed throughout the near infrared spectrum and coefficients and equations relating the measurable characteristics to each measurement are developed by linear regression. While the above technique of analyzing materials have proved to be effective and accurate, there are inaccuracies in the measurements which occur in part because the mathematical pretreatment applied to the data doesn't perfectly linearize the data. The assumption of linear regression is that absorption fractions determined for the material relate directly to the concentrations of the absorbers in the material. In real material samples, physical factors, such as inhomogeniety, packing density, and particle size, affect the relationship between the absorption fractions determined for the sample and the concentrations of absorbers in the sample. To the extent these factors vary from sample to sample, increased uncertainty in concentration estimates results compared to the case where their variation is absent. The error caused by these factors is often small compared to other sources of error but cases in which packing or particle size variations visibly affect spectra are frequently encountered. Accordingly, there has been an effort to generate functions which describe the system of reflection from and transmission through the material theoretically and then use these functional forms as a guide in setting up regression analysis. One such theoretical description is the widely used Kubelka-Munk equation, which has a theoretical basis and provides a linear function for the remission function. The Kubelka-Munk equation for remission is:

$$F(R)=(1-R)^2/2R=K/S=2k/2b$$

In this equation, R is the remission fraction from a sample of infinite thickness, and F(R) has been called the remission function. K and S are the Kubelka-Munk absorption and scattering coefficients. The linear coefficients for absorption and remission are given by k and b.

The Kubelka-Munk theory was developed for dense materials. They drew from work on a rather different kind of system which was examined in 1905 by Schuster in an article entitled "Radiation Through a Foggy Atmosphere". A. Shuster, *Astrophysical* J. 21, 1 of (1905). In summarizing the application of this work to reflectance spectroscopy, Kortum describes remission as a function of absorption and scattering coefficients. G. Kortum, *Reflectance Spectroscopy* (Springer-Verlag, New York, N.Y. 1969.) Using the reported definitions for the coefficients, the following equation is obtained:

$$F(R)=[2\alpha/(\alpha+\sigma)]/[\sigma/(\alpha+\sigma)]=2\alpha/\sigma$$

This equation is referred to as the Shuster-Kortum equation. Kortum terms $\alpha$ and $\sigma$ as the "true absorption" and scattering coefficients of "single scattering". Alternatively $\alpha$ and $\sigma$ can be interpreted to be the relative probabilities (fractions) of absorption and scattering respectively for the light which interacts with a single particle.

The above equations, and modifications thereof presented by several other authors, were derived using continuous functions and are collectively referred to as continuum theories. It is believed that the continuum theories are not completely satisfactory, since the scattering coefficient and absorption coefficient refer to units of thickness of homogeneous layers treated as a continuum whereas most material samples are not homogeneous and typically are made up of particles.

Discontinuum theory, sometimes called the statistical method, is quite distinct from the continuum theories in the sense that an actual summation is carried out over the fundamental units of which the absorbing and light-scattering sample is composed. Heretofore, discontinuum theory had limited application because it was applied only to a specific model for the particular sample under consideration. However, it has been recognized that such methods can provide a relationship between the fundamental constants of the particles and the measurable quantities. In this invention, this benefit is extended to a more general case.

The Equations of Benford

The following discussion and equations constitute an example of the discontinuum approach. While some of the equations can be attributed to many different sources, a very complete treatment of the equations is given by Benford; F. Benford, *J. Opt. Soc. Am.* 36, 524 (1946).

In Benford's treatment, a sample of material is divided into rectangular layers of finite thickness, as shown in FIG. 3. Radiation entering a given layer may be absorbed, may be transmitted forward into the next layer, or may change direction and be remitted into the previous layer. The fractions of light absorbed, transmitted, and remitted from a particular layer, i, are given by the symbols $a_i$, $t_i$ and $r_i$, respectively. The subscript of a symbol designates the layer to which the symbol applied. If a second layer, j, is added, a fraction (of the incident intensity) $t_i$ enters layer j, and a fraction $t_i t_j$ will be transmitted through both. A fraction $t_i r_j$ will be remitted by the second layer back into the first. It may, then, either be transmitted through the first layer (and recorded as part of the total reflected light), absorbed in the first layer, or remitted back into the second layer. This remission back and forth between layers in a sample can continue indefinitely. The overall forward and backward flux and absorption for a material which is composed of two layers, i and j, is given by the following equations:

$$t_{i+j}=t_i t_j/(1-r_i r_j) \quad r_{i+j}=r_i+t^2_i r_j/(1-r_i r_j) \quad a_{i+j}=1-t_{i+j}-r_{i+j} \tag{1}$$

Let it be supposed that a homogeneous sample is divided into many identical layers and the properties of a single layer are given by $t_1$, $r_1$ and $a_1$ The properties of a sample consisting of i+1 of these layers can be derived from the properties of a sample consisting of i of these layers, as follows:

$$t_{i+1}=t_i t_1/(1-r_i r_1) \quad r_{i+1}=r_i+t_i^2 r_1/(1-r_i r_1) \quad a_{i+1}=1-t_{i+1}-r_{i+1} \tag{2}$$

For a sample one half as thick as a known sample i:

$$r_{i/2}=r_i/(1+t_i) \quad t_{i/2}=[t_i(1-r_{i/2}^2)]^{1/2} \quad a_{i/2}=1-t_{i/2}-r_{i/2} \tag{3}$$

For a sample twice as thick as a known sample i:

$$t_{2i}=t_i^2(1-r_i^2) \quad r_{2i}=r_i(1+t_{2i}) \quad a_{2i}=1-t_{2i}-r_{2i} \tag{4}$$

These equations are employed in the present invention.

SUMMARY OF THE INVENTION

In accordance with the present invention, the Benford equations are used to calculate the absorption coefficient and the remission coefficient of a material at each wavelength in the spectrum. The absorption coefficient is defined as the absorption fraction of a very thin layer divided by the thickness of the very thin layer wherein the layer is thin enough that the absorption from the layer is not affected by remission from the layer. The remission coefficient is defined as the remission fraction from a very thin layer divided by the thickness of the very thin layer wherein the very thin layer is thin enough that the remission from the layer is not affected by the absorption of the layer. The absorption coefficient for most material samples is linearly related to the concentrations of the absorbers in the sample and therefore can be used to make an accurate determination of the concentration of the absorbers in the material of the sample. Similarly the remission coefficient is linearly related to the particle sizes in the material, and accordingly can be used to make an accurate determination of the particle sizes of different types of particles in the material as well as to make a determination of properties of the material related to particle size. In accordance with the invention, the absorption and remission coefficients are calculated by using the Benford equations for remission fractions and absorption fractions from a layer of one-half the thickness of the sample layer and then repeating this calculation on the results obtained for the half-thickness layer until the determined absorption fractions and remission fractions reach limiting values which occurs when the determined absorption fraction is one-half the absorption fraction obtained in the previous calculation and the remission fraction is one-half the remission value obtained in the previous calculation. The absorption and the remission coefficients can then be determined by dividing these absorption and remission fractions by the thickness of the layer.

DESCRIPTION OF THE PREFERRED EMBODIMENT

Figure 1:
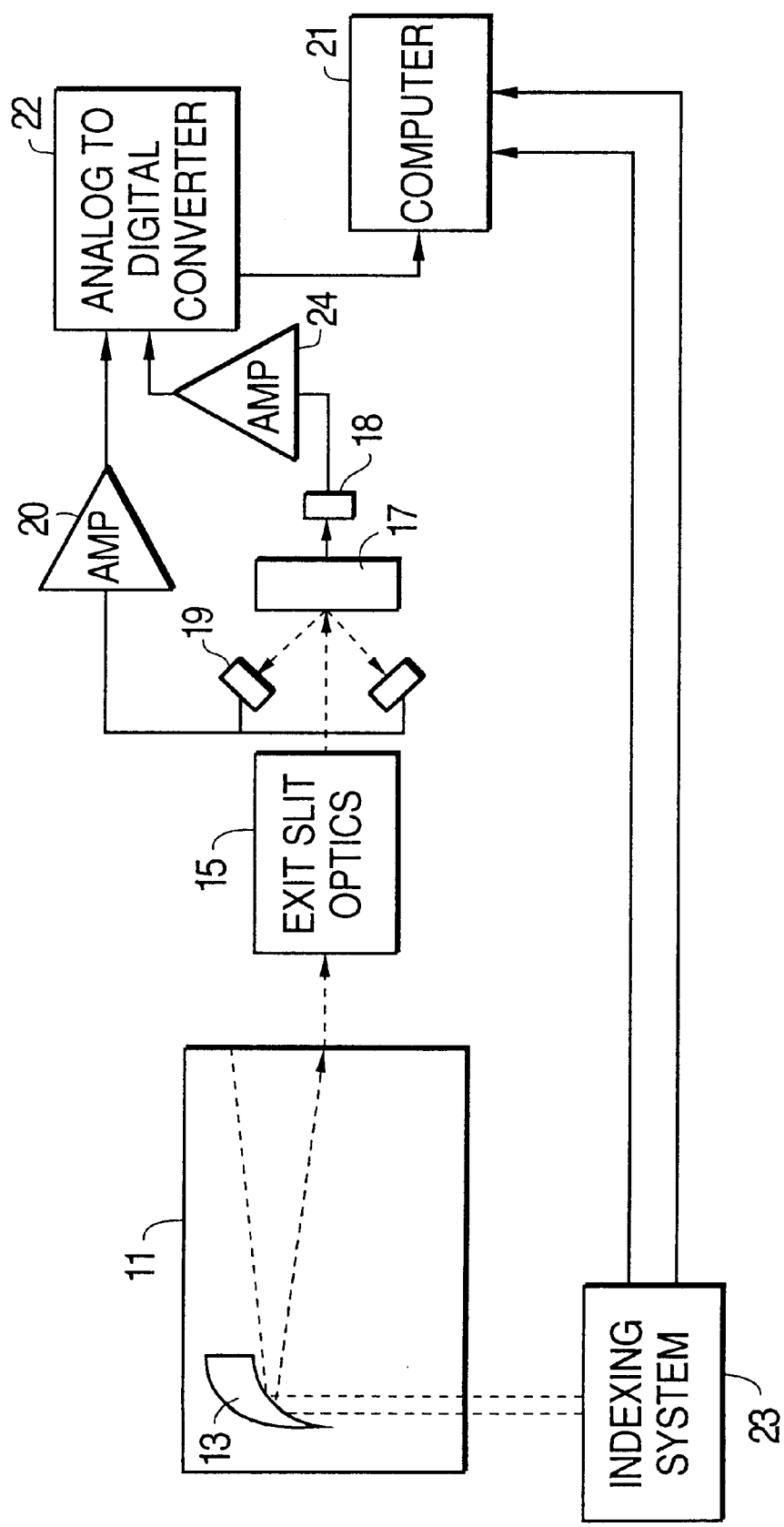
FIG. 1 illustrates an instrument in which the present invention is employed.

As shown in FIG. 1, the apparatus employed in the system of the present invention comprises an infrared spectrometer 11 having an oscillating grating 13 on which the spectrometer directs light. The grating 13 reflects light with a narrow wavelength band through exit slit optics 15 to a sample 17. As the grating oscillates, the center wavelength of the light that irradiates the sample is swept through the near infrared spectrum. Light from the diffraction grating that is reflected by the sample is detected by near infrared photodetectors 19. The light transmitted through the sample is detected by a photodetector 18. The photodetectors 19 generate a signal representing the intensity of the reflected light. This signal is transmitted to an analog-to-digital converter 22 by amplifier 20. Photodetector 18 generates a signal representing the intensity of the light transmitted through the sample. This signal is transmitted to analog to digital converter 22 by amplifier 24. An indexing system 23 generates pulses as the grating 13 oscillates and applies these pulses to a computer 21 and to the analog-to-digital converter 22. In response to the pulses from the indexing system 23, the analog-to-digital converter converts successive samples of the output signal of the amplifiers 20 and 24 to digital values. Each digital value corresponds to the reflectivity or transmissivity of the sample at a specific wavelength in the near infrared range. The computer 21 monitors the angular position of the grating 13 and accordingly monitors the wavelength irradiating the sample as the grating oscillates, by counting the pulses produced by the indexing system 23. The pulses produced by the indexing system 23 define incremental index points at which values of the output signal of the amplifier are converted to digital values. The index points are distributed incrementally throughout the near infrared spectrum and each corresponds to a different wavelength at which the sample is irradiated. The computer 21 converts reflectivity value and transmissivity value at each wavelength to an absorption coefficient of the material and a remission coefficient in the manner as described below.

The Dahm Equation:

Let it be assumed that there is a sample which is infinitely thick and which is made up of many layers identical to the first (for which the fraction absorbed, remitted, and transmitted are given by a, r, and t). An Absorption/Remission Function, A(R), for remission from an infinitely thick sample is defined as:

$$A(R)=(1-R)^2/R=a_\infty^2/r_\infty A(R)=2F(R) \qquad (5)$$

For any given absorption, remission and transmission fractions for a single layer, the R of a material may be obtained from the Equations of Benford by repetitively calculating $r_i$ for doubling of thickness. The limiting value of $r_i$ gives R for the sample material for which the following relationships hold. These relationships are referred to as the Dahm Equations.

$$A(R) = (2-a-2r)a/r = (1+t-r)a/r \quad F(R) = (1-a/2-r)a/r$$
$$a = 1 - r - ((1-r)^2 - r*A(R))^{1/2} \qquad r = a(2-a)/(2a+A(R))$$

(6)

Comparison of the Dahm Equation with Kubelka-Munk:

The Kubelka-Munk equation was derived using continuous functions. The stated assumptions of Kubelka-Munk theory include the assumption that samples are homogeneous and the assumption that the particles are small. In reality, the mathematics used in the Kubelka-Munk theory assumes that the particles are infinitesimal, that each point in a sample of material is exactly like every other, except for position. A sample is assumed to have a flat front surface and extend infinitely in all other directions. Light moves forward into the sample from outside the sample surface. As light of a given intensity moves through a very thin layer (bounded by two planes parallel to the sample surface), a certain fraction of it, a, will be absorbed, and a certain fraction of it, r, will reverse direction. This reversing of direction gives rise to a light flux in the backward direction, which is subject to the same fate as the forward flux. Under these conditions, Kubelka and Munk showed that the absorption of the material (as measured by the Kubelka-Munk function) is dependent on the ratio a/r, and is not dependent on the magnitude of a or r. This may be expressed mathematically as F(R)=a/r. In order to apply the results of their equation to real samples, Kubelka and Munk expressed their results not in terms of fractions of light, but in terms of coefficients. (The linear absorption coefficient of a material is defined as the fraction of light absorbed by a very small thickness of a material divided by the magnitude of that small thickness.)

For very thin layers, the values of a and r will be very small compared to 1, and the Dahm equation becomes identical to the Kubelka-Munk Equation. It is this situation of small particles with low absorption, where the K-M Theory has been found to hold. The criterion used to make this determination was usually that a plot of F(R) vs. concentration of absorber be linear. However, the Dahm equation shows that when transmission loss through a single particle is significant, A(R) is dependent on the magnitudes of the absorption and scattering fractions, as well as their ratio. Thus, the Dahm equation can be expected to apply to some highly absorbing systems for which the K-M Theory fails.

Comparison of the Dahm Equation with Schuster-Kortum:

Schuster examined the case of very dilute suspension of particles. In "a foggy atmosphere", the volume fraction of particles is small, and the distance between particles is large compared to the size of the particles. In the limit, a single particle may be considered to be in each layer. Almost none of the light passing through a layer one particle wide would be absorbed or scattered; rather almost all of the light would be transmitted through the plane. The fraction of light which passes through the layer without interacting with any particle may be given by T. Of the light which interacts with the particle in the layer, the fraction, $\alpha$, is absorbed and the fraction, $\sigma$, is assumed to be scattered isotopically. Consequently, $\alpha+\sigma+T=1$. For such a system, $F(R)=(1+T)\alpha/\sigma$. For very dilute systems T is very nearly 1, and the Dahm and Schuster-Kortum equations become identical.

The Dahm equation can be expected to apply to samples which are of much higher density than can the Schuster Equation. For dense systems, the $\alpha$ is replaced by a, and $\sigma$ is replaced by 2r. The ratio $\alpha$ is equal to a/2r only if there is no possibility of multiple scattering within the layer.

Obtaining Absorption and Remission Coefficients

The absorption and remission coefficients for a material are of significantly more value than the fractions (a, r and t) for an arbitrarily defined layer. The absorption coefficient can be expected to relate linearly to concentrations of absorbers in the material for homogenous materials and for materials made up of small particles having relatively low absorption coefficients as will be shown below.

Let it be assumed that a sample is a very thin layer having thickness $d_o$. Let the fraction of light remitted by this layer be $r_o$, and the fraction of light absorbed be $a_o$. For a very thin layer, the fraction of light remitted is not significantly affected by the amount of light absorbed and vice versa. Then an absorption coefficient, k, may be given by $a_o/d_o$. Similarly, a remission coefficient, b, may be given by $r_o/d_o$. The absorption and remission coefficients for a sample can be derived from the values of a, r and t for larger thicknesses by repetitively calculating the values $a_{i/2}$ and $r_{i/2}$ for half thickness. When the calculated value for $a_{i/2}$ is exactly one half of $a_i$ (to as many significant figures as desired) the limiting slope has been reached and $a_i/d_i$ gives the linear absorption coefficient, k, for the material. Similarly, when the calculated value for $r_{i/2}$ is exactly one half of $r_i$, $r_i/d_i$ gives the linear remission coefficient, b, for the material.

In theory, it is possible to measure r and t for a sample of finite thickness and obtain a by difference (a=1−r−t). If the thickness is known, the coefficients may be calculated as explained above. Sometimes, it may be difficult to measure r and t on the same absolute scale. In such cases, either r or t values may be measured at the same wavelength for two samples of different thicknesses of the same material. Given r values for two thicknesses, one can calculate t and a by use of Benford's equations as well as the constraint a+r+t=1. Similarly, a and r values can be derived from t values for two different sample thicknesses. This calculation is discussed in detail in Benford's article F. Benford, *J. Opt. Soc. Am.* 36, 524 (1946).

The Representative Layer:

The above description explains how to calculate an absorption coefficient for a material from the properties of an idealized homogenous layer. However, a typical sample of a material to be analyzed is made of particles. In order to measure the concentration of certain components in such a material, there must be developed a model which relates to the absorption coefficients of these components of interest to the properties of a representative layer of the material. In certain situations, this auxiliary model may embody assumptions which result in a poor description of reality, but that failure would not invalidate the Dahm Equation. The Dahm Equation, along with the Equations of Benford from which it can be derived, is believed to be an exact solution for layers whose absorption and scattering properties are fully defined. The Dahm equation and the Kubelka-Munk equation are both exact solutions for the situation they describe. The difference is that the Dahm equation better describes systems of finite particles than does the Kubelka-Munk.

In this model, the samples will be considered to be made up of small particles, which have no interfaces other than the particle's external surface, and it will be presumed that all interfaces are between the medium (usually air) and the particle surface. When particles are poured into a sample container with flat parallel sides, by definition a sample of uniform thickness is produced. It may have voids and consist of particles of different sizes and shapes, but it has a uniform thickness. The properties of a representative layer of such a sample will now be considered.

Figure 2A:
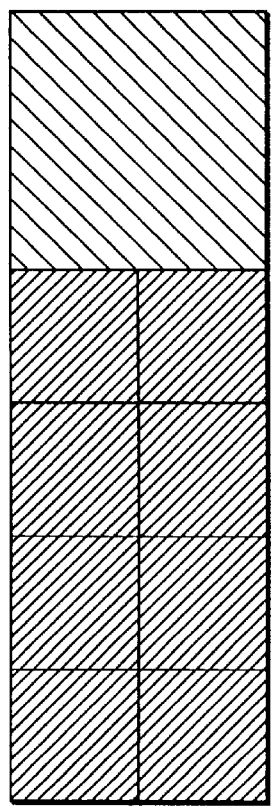
FIG. 2(*a*) and 2(*b*) are a top view and a side view of a theoretical layer of particles from a sample and from which the theory of the present invention is derived.
Figure 2B:
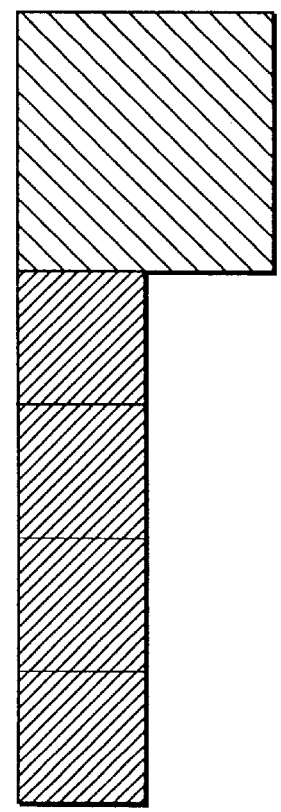
Figure 3:
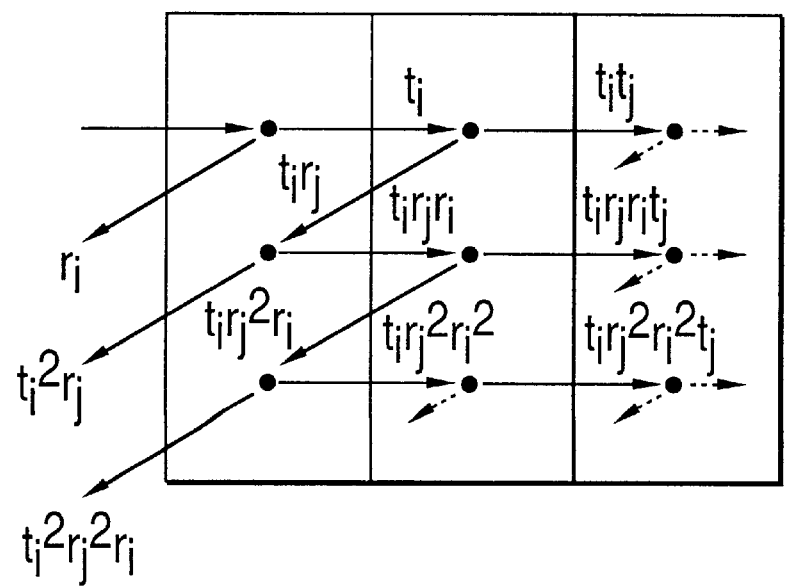
FIG. 3 diagrammatically illustrates the transmission and remission action that occurs from theoretical adjacent layers of the sample.

In this analysis, the layer is not required to be of uniform thickness. It will consist of a single layer of particles, some larger (and therefore thicker) and some smaller, and of voids. It will be assumed that these layers can somehow fit together to make the sample have its uniform thickness, but the sample will be envisioned as well separated layers. The sample will be considered to have a variety of particle types in the sample. The particles may be of a different type because they have different composition or because they have a different size. In the representative layer, it will be required that a) each particle type occupies the same fraction of the total volume of the layer that it occupies in the sample; b) the void fraction is the same in the representative layer as in the sample as a whole; c) the fractions of cross-sectional area of each particle type in the representative layer will be in the same proportion as the surface area of each type in the sample as a whole; and d) the fraction of cross-sectional area in the representative layer made up by voids will be the same as the void fraction in the sample as a whole. FIG. 2a show a top view of an example of a representative layer and FIG. 2b shows a side view of the representative layer of FIG. 2a.

It will be seen in the following mathematical section that for samples of small particles of low to moderate absorption, the following approximations result.

1) The contribution of a particle type to absorption is proportional to the volume fraction (including voids) of the particle type and to the absorption coefficient of the material making up the particle.

2) The contribution of a particle type to remission is proportional to the cross sectional surface area of the particle type in the representative layer and the scattering power of the material making up the particle.

For particles with higher absorption, the contribution of a particle to the absorption of a layer is determined by the Bouguer-Lambert Law, with an exponential fall-off of transmitted intensity across the thickness of the particle.

Mathematical Expression of Model:

In the following, i is an subscript denoting a specific particle type, and j is an index denoting a summation over all particle types. It is assumed that all particles are cubes with one face perpendicular to the incident light beam.

$d_i$—the length of the edge of a particle of type i.
$d_i^2$—the cross sectional surface area of a particle of type i.
$d_i^3$—the volume of a single particle of type i.
$p_i$—density of a particle of type i.
$w_i$—weight fraction of a particle of type I.
$v_o$—void fraction of the sample.
$v_i$—fraction of occupied volume composed of particle type i.
$V_i$—fraction of total volume composed of particle type i.
$S_i$—fraction of particle surface area which belongs to particle type i.
$S_i$—fraction of a cross-sectional surface which will be comprised of particles of type i.
$K_i$—the absorption coefficient of the material comprising particle type i.
$b_i$—the remission coefficient of the material comprising particle type i.
$(bd)_i$—the remitting power of the material comprising particle type i.

For any plane passed through the sample, $S_i$ is the fraction made up of particle type i.

The relationship between surface area and volume fraction is given by:

$$s_i = (v_i/d_i)/\Sigma(v_j/d_j) \quad S_i = (1-V_o)(v_i/d_i)/\Sigma(v_j/d_j) \quad (8)$$

The amount of the material of a particular type in a sample is usually expressed in terms of weight fraction.

Then:
$$v_i = (w_i/p_i)/\Sigma(w_j/p_j) \quad s_i = (w_i/p_id_i)/\Sigma(w_j/p_jd_j) \quad (7)$$
$$V_i = (1-v_o)(w_i/p_i)/\Sigma(w_j/p_j) \quad S_i = (1-v_o)s_i$$

The following formulas assume that the amount of transmitted light lost by an interaction with a single particle either to absorption or remission is small.

For a single particle the fraction of light absorbed is given by the cross sectional area and the Bouguer-Lambert Law, and the remission fraction is given by the cross sectional area and $b_i d_i$. Thus, for a representative layer:

$$a = \Sigma S_j[1 - \exp(-K_i d_i)] \quad (9)$$
$$r = \Sigma S_j b_j d_j$$

When $K_i d_i$ is small for all particle types, the following approximation can be made:

$$a = \sigma S_j K_j d_j \quad (10)$$

Then:

$$a = \Sigma V_j K_j /\Sigma(v_j/d_j) \quad (11)$$

These equations are the basis for the approximation stated above that the contribution of a particle type to absorption is proportional to the volume fraction (including voids) of the particle type and to the absorption coefficient of the material making up the particle. This being the case, the Dahm equations apply and the technique of determining the absorption coefficient by repeatedly dividing the thickness of the layer in half until the absorption coefficient reaches the limiting value is applicable to samples of small particles of low to moderate absorption.

It has been shown experimentally that $b_j$ is proportional to $1/d_i$. This is equivalent to saying that remission fraction is proportional to surface area, and follows from the assumption that the remission fraction is a property of an interface. For the moment, it is sufficient to note that this implies that the product $b_i d_i$ is a property of the composition of the particle but is independent of particle size. Thus, $(bd)_i$ is defined as the remitting power of a material, and the following expression is:

$$r = \Sigma S_j \, (bd)_j \tag{12}$$

This equation is the basis for the approximation stated above that the contribution of a particle type to remission is proportional to the cross sectional surface area of the particle type in the representative layer and the scattering power of the material making up the particle.

ANALYSIS OF AN UNKNOWN SAMPLE

To analyze an unknown material, that is to determine the percentage concentrations of components of the sample, the reflectance and transmittance spectra from a set of known samples, preferably similar to the unknown material, are measured using the instrument of FIG. 1. In the known samples, the percentage constituents of interest to the analyzer are known. From these spectra, the spectra of absorbent coefficients and the spectra of a remission coefficients are determined by the computer 21 for the known samples, one spectrum of absorbent coefficients and one spectrum of remission coefficient being determined for each known sample. The appendix attached hereto contains a source code listing in Array Basic of the computer program for determining the spectra absorbance and remission coefficients from the measurements made from the sample, making use of the Benson equations described above and the technique of dividing the width of the sample repeatedly in half until the absorption and remission coefficients reach a limiting value. The spectra of absorption coefficients for the known samples can then be used to determine the percentage constituents in the unknown material. For a particulate sample in which all the particles are of the same type, the absorption coefficient $k_j$ of the sample at any given wavelength J can be expressed as follows:

$$k_j = (1 - V_{on}) \Sigma_{(I)} E_{IJ} C_I \tag{13}$$

in which $E_{IJ}$ is the absorption coefficient of absorber I in the sample, $C_I$ is the concentration of absorber I (relative to the occupied volume) in the sample, and $V_{on}$ is the void fraction of the sample. For a sample containing particles of different types, the absorption coefficient $k_j$ can be expressed as follows:

$$k_j = (1 \oplus V_{on}) \Sigma_{(M)} \Sigma_{(I)} E_{IJ} C_{IM} V_M \tag{14}$$

in which M represents a particle type, $C_{IM}$ is the concentration of absorber I in particle type M an $V_M$ is the volume fraction of particle M in the occupied volume. To determine the concentration of absorbers in an unknown sample, the absorption coefficient is determined, in the manner described above, for a set of known samples, in which the concentrations of the absorbers is known, at several wavelengths distributed throughout the spectrum. The absorption coefficients are also determined for the unknown material. Then using equation (13) or (14), the concentration of the absorber in an unknown material is determined by linear regression.

In this process, the concentration of the absorber of the interest for the known samples are represented in a set of equations as follows:

$$C_1 = U_0 + U_1 k_{11} + U_2 k_{12} + \ldots U_n k_{1m} \tag{15}$$
$$C_2 = U_0 + U_1 k_{21} + U_2 k_{22} + \ldots U_m k_{2m}$$
$$C_3 = U_0 + U_1 k_{31} + U_2 k_{32} + \ldots U_m k_{3m}$$
$$C_4 = U_0 + U_1 k_{n1} + U_2 k_{n2} + \ldots U_m k_{nm}$$

In these equations, $C_1$ is the percentage concentration of an absorber of interest in the first known sample. $C_2$ is the concentration of this absorber in a second known sample and $C_3$ is a concentration of this component in the third known sample and $C_n$ is a concentration of this component in the nth sample. $k_{11}$ through $k_{1m}$ represent the absorption coefficient spectrum determined for the first known sample distributed throughout the near infrared spectrum. $k_{21}$ through $k_{2m}$ represent the absorption coefficient spectrum determined for the second known sample. $k_{31}$ through $k_{3m}$, represent the absorption coefficient spectrum for the third known sample, and $k_{n1}$ through $k_{nm}$ represent the absorption coefficient spectrum for the nth known sample. From these equations, the coefficients $U_0$ through $U_m$ are determined by multiple regression or by least squares analysis. The reflectance and transmittance spectra then measured from a sample of the unknown material and then using the program in the appendix the spectrum of absorption and remission coefficients are determined for the unknown material. The concentration $C_X$ of the constituent of interest is then determined for the unknown sample from the following equation:

$$C_x = U_0 + U_1 k_{x1} + U_2 k_{x2} \ldots U_m k_{xm} \tag{16}$$

In this equation, $k_{x1}$ through $k_{xm}$ is the absorption coefficient spectrum for the unknown material and the coefficients $U_0$ through $U_m$ are the coefficients determined from the equations (15) for $C_1$ through $C_n$, representing the concentrations of the constituent in the known samples.

Additional percentage concentrations of other constituents in the unknown sample can be determined in a similar manner from the known concentrations of such other constituents in the known samples and using multiple regression equations to determine the coefficients for the equation for each constituent to be analyzed in the unknown sample.

Equation (14) can also be used to determine the concentration of particle type in unknown samples assuming the concentrations of the particle types in known samples are known.

The remission coefficients may be used in a similar manner to determine the particle size of each particle type in the sample. These calculations would also be expected to be useful in determining physical properties of a sample related to particle size.

If the unknown sample is made up of relatively larger or more highly absorbent particles, Equations (13) and (14) will not provide an accurate representation of the absorption coefficient of the material of the sample and instead equations derived from Equation (9) must be used. This means that the contribution of particle type to absorption will not be proportional to the volume fraction of the particle type and to the absorption coefficient of the material making up the particle. This nonlinearity in such samples would be expected to introduce errors into the analysis of a sample by linear regression. However, if the known samples are similar enough in particle type, particle size, and packing density to the unknown material, these errors will be compensated for by the linear regression process. If the known samples are not sufficiently similar to the unknown material, the analysis can still be carried out by nonlinear regression using the following equations for the absorption coefficient as a model:

$$k_j = \Sigma_{(M)} \Sigma_{(I)} S_M [1 - \exp(E_{IJ} C_{IM} D_M)]$$

In this equation, $S_M$ is the cross-sectional surface area fraction of a particle of type M and $D_M$ is the thickness of the particle of type of M.

In the system of the invention, the absorption coefficients and the remission coefficients are determined in accordance with a discontinuum theory as represented by Benford's equations. As a result, when these coefficients are used to determine measurable characteristics such as percentage of constituents, the measurements are not adversely affected by inhomogeniety and variations in packing density and particle sizes in the samples and, as a result, more accurate measurements are obtained.

We claim:

1. A method of determining the absorption coefficient of a material comprising providing a sample of said material, having a finite thickness, making reflectance and/or transmittance measurements on said sample, determining the remission fraction of said sample, the transmission fraction of said sample and the absorption fraction of said sample from the measurements of reflectance and/or transmittance, and repeatedly determining from the previously determined fractions of remission, transmission and absorption, the remission fraction, the transmission fraction, and the absorption fraction of layers of said material having thicknesses which in each repetition are a smaller thickness of said material until the quotient of the absorption fraction divided by the thickness of the layer reaches a limiting value wherein said quotient is the absorption coefficient of the material.

2. The method as recited in claim 1, wherein in each repetition of the step of repeatedly determining the remission fractions, transmission fraction and absorption fraction, the thickness of the layer is one-half the thickness of the layer in the preceding repetition.

3. A method as recited in claim 1, wherein the remission fraction, transmission fraction and absorption fraction of each layer having a smaller thickness is determined by equations corresponding to a discontinuum theory of absorption, remission and transmission.

4. A method as recited in claim 1, wherein the absorption coefficient for said sample is determined for a multiplicity of different wavelengths in the near infrared spectrum.

5. A method as recited in claim 4, wherein said multiplicity of wavelengths are incrementally distributed throughout the near infrared spectrum.

6. A method of determining the concentration of an absorber in an unknown material comprising making the absorption coefficient determinations on known samples as recited in claim 4, said known samples each having a known concentration of said absorber, making absorption coefficient determinations on a sample of said unknown material as recited in claim 4, and determining the concentration of said absorber in said unknown material sample by regression analysis from the absorption coefficients determined for said known samples.

7. A method of determining the remission coefficient of a material comprising providing a sample of said material having a finite thickness, making reflectance and/or transmittance measurements on the sample, determining the remission fraction of said sample, the transmission fraction of said sample and the absorption fraction of said sample from the measurements of reflectance and/or transmittance, repeatedly determining from the previously determined fractions of remission, transmission and absorption, the remission fraction, transmission fraction and absorption fraction of layers of said material having thicknesses which in each repetition are a smaller thickness of the material until the quotient of the remission fraction of a layer of said material divided by its thickness reaches a limiting value wherein the limiting value of said quotient is the remission coefficient of said sample.

8. The method as recited in claim 7, wherein in each repetition of the step of repeatedly determining the remission fraction, transmission fraction and absorption fraction, the thickness of the layer is one-half the thickness of the layer in the preceding determination.

9. A method as recited in claim 7, wherein the remission fraction, transmission fraction, absorption fraction of each layer having a smaller thickness is determined by equations corresponding to a discontinuum theory of absorption, remission, and transmission.

10. A method as recited in claim 7, wherein the remission coefficient for said sample is determined for a multiplicity of different wavelengths in the near infrared spectrum.

11. A method as recited in claim 10, wherein said multiplicity of wavelengths are incrementally distributed throughout the near infrared spectrum.

12. An apparatus for determining the absorption coefficient of a sample at different wavelengths comprising means to illuminate said sample with light including said different wavelengths, means to detect the intensity of the light reflected from and/or transmitted through said sample at said different wavelengths, computer means to determine from the detected intensities of light transmitted and/or reflected from said sample, the remission fractions, absorption fractions, and transmission fractions of said sample at said different wavelengths, and to determine the absorption coefficients of the material of said sample at said different wavelengths from the determined fractions of remission, transmission and absorption by means of equations relating to the remission, absorption and transmission fractions of layers of different thicknesses in accordance with a discontinuum theory.

13. An apparatus for determining remission coefficients of a sample at different wavelengths comprising means to illuminate said sample with light including said different wavelengths, means to detect the intensity of light reflected from and/or transmitted through said sample at said different wavelengths, computer means to determine from said detected intensities, the remission, absorption and transmission fractions of said sample and to determine the remission coefficients of the material of said sample from the determined fractions of remission, absorption and transmission by means of equations relating to remission, absorption and transmission of layers of different thicknesses in accordance with a discontinuum theory.

* * * * *

UNITED STATES PATENT AND TRADEMARK OFFICE
CERTIFICATE OF CORRECTION

PATENT NO. : 5,912,730
DATED : June 15, 1999
INVENTOR(S) : Donald J. Daum et al.

It is certified that error appears in the above-identified patent and that said Letters Patent is hereby corrected as shown below:

Column 8, line 57, change equation (10) to read:

$$a = \Sigma S_j K_j d_j$$

Column 9, line 14, change equation (14) to read:

$$k_j = (1-V_{on})\Sigma_{(M)}\Sigma_{(I)}E_{(IJ)}C_{IM}V_M \tag{14}$$

Column 10, line 15, change the last line of equation (15) to read:

$$C_n = U_o + U_1 k_{n1} + U_2 k_{n2} + ... U_m k_{nm}$$

Signed and Sealed this

Twenty-third Day of May, 2000

Attest:

Q. TODD DICKINSON

*Attesting Officer*      *Director of Patents and Trademarks*